(12) United States Patent
Ferguson et al.

(10) Patent No.: US 6,623,694 B1
(45) Date of Patent: Sep. 23, 2003

(54) NON-FOAMING WATER FOUNTAIN AND COMPOSITION

(75) Inventors: John A. Ferguson, Westerville, OH (US); Kristin Prince, Westerville, OH (US)

(73) Assignee: Bath & Body Works, Inc., Reynoldsburg, OH (US)

( * ) Notice: Subject to any disclaimer, the term of this patent is extended or adjusted under 35 U.S.C. 154(b) by 220 days.

(21) Appl. No.: 09/650,291

(22) Filed: Aug. 29, 2000

(51) Int. Cl.$^7$ ............................................... A61L 9/00
(52) U.S. Cl. ................................. 422/5; 422/1; 239/20
(58) Field of Search .................... 239/17, 18, 20–23; 422/5, 1, 3; 252/174.15, 174.21, 174.22

(56) References Cited

U.S. PATENT DOCUMENTS

| | | | | |
|---|---|---|---|---|
| 3,644,726 A | * | 2/1972 | Pfeuffer | 240/10 R |
| 4,519,914 A | * | 5/1985 | Etani | 210/633 |
| 4,591,094 A | * | 5/1986 | Morris | 239/17 |
| 4,705,216 A | * | 11/1987 | Kaffka et al. | 239/18 |
| 4,983,316 A | * | 1/1991 | Starch | 252/174.15 |

FOREIGN PATENT DOCUMENTS

| | | | |
|---|---|---|---|
| CA | 1047693 A | * | 12/1990 |
| DE | 19624439 A1 | * | 1/1998 |
| FR | 2663846 A | * | 1/1992 |

* cited by examiner

Primary Examiner—Robert J. Warden, Sr.
Assistant Examiner—Sean E. Conley
(74) Attorney, Agent, or Firm—Colucci & Umans; Peter C. Michalos; Angelo Notaro

(57) ABSTRACT

A fragrant, non-foaming emulsified composition has a siloxane anti-foam agent and water solution, a block co-polymer, denatured 200 proof alcohol and fragrance oil. Alternative compositions contain a solubilized fragrance or an insoluble fragrance oil for adding to water. The compositions may be provided in a concentrated form, for addition to a pre-existing water supply in a recirculating fountain, or in a dilute form for use as the recirculating fluid in the fountain. The compositions are clear and do not foam when used in a recirculating fountain. The compositions provide fragrance at a release rate significantly greater than solid or gel air fresheners with the same concentration of fragrance. Methods of fragrancing a room with the compositions are disclosed as well.

17 Claims, 1 Drawing Sheet

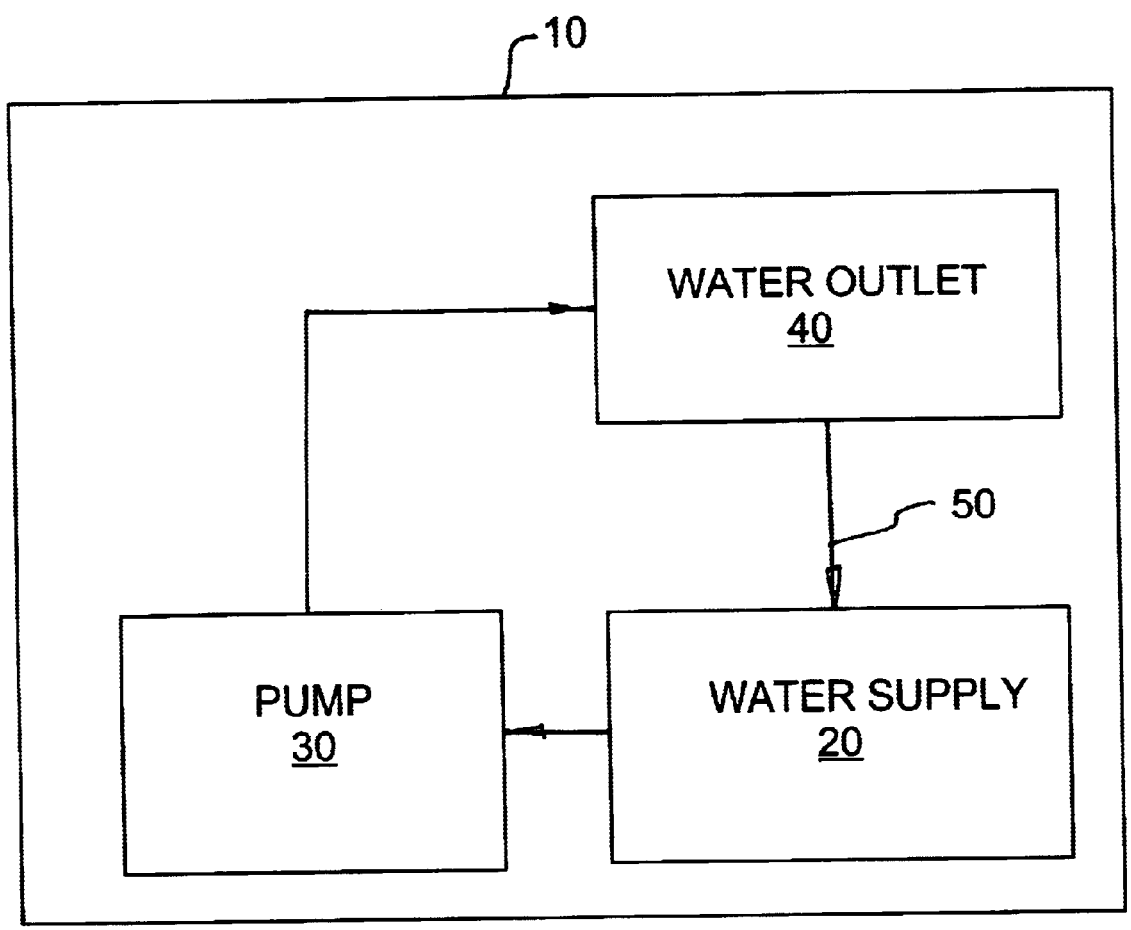

NON-FOAMING WATER FOUNTAIN AND COMPOSITION

FIELD AND BACKGROUND OF THE INVENTION

The present invention relates generally to the field of air fresheners and in particular to a new and useful water soluble perfumed composition which can be used in a moving water display without foaming.

Portable display fountains are known for use, such as taught by U.S. Pat. No. 6,029,899 for a table top fountain. The fountain has a fluid container with a waterproof recirculating pump mounted inside. A column open at the ends extends upwardly from a part of the bottom of the container. A power cord for the pump passes through the column. A rubber plug is used to seal the open upper end of the column so that water does not leak out of the container.

Portable or table top recirculating fountains like that of U.S. Pat. No. 6,029,899 are typically used to provide a relaxing display, like a fish tank, for a person. These fountains can be used in homes or in offices. The sound of the water moving through the fountain can be both pleasing and relaxing. In addition, the fountain can have desirable design features, making it a useful ornamental piece in the room where it is located.

While the sound and appearance of recirculating fountains are known and have been used for relaxation, until now a third pleasing and useful element—fragrance—has not been available for use in water-based fountains without severe problems.

Attempts to fragrance moving water, such as found in a recirculating fountain, have resulted in the water foaming and creating an unacceptable appearance in the fountain and incompatibility with fountain parts and components, such as melting plastic fountain parts. At the same time, the amount of fragrance released from the fountain has been poor, with scented fountains providing almost no scent compared to other air freshening devices.

The combination of water soluble fragrance oils with water tends to cause foaming when the mixture is agitated, primarily due to the unavoidable presence of impurities and/or surfactants in the mixture. Silicone-based anti-foaming agents, while well known for preventing the formation of foam in mixtures containing surfactants, produce a cloudy mixture. Further, the scent release problem has not been addressed by the prior compositions.

Clear scented compositions for other purposes are known, such disclosed in U.S. Pat. No. 4,983,316 for a relatively clear detergent with controlled foaming behavior having a dispersable silicone anti-foaming agent. The silicone anti-foaming agent is a mixture of two anti-foam agents, the primary anti-foaming agent being a mixture of a polyorganosiloxane, a resinous siloxane, a finely divided filler material and a catalyst to promote the reaction of the elements. The secondary anti-foaming agent is a mixture of a polydimethylsiloxane fluid, a nonionic silicone surfactant and two dispersing agents. One of the dispersing agents may be an ethylene oxide/propylene oxide block co-polymer.

U.S. Pat. No. 5,968,889 teaches a detergent having anti-foam properties. A silicone anti-foaming agent is combined with a carboxylated poly(oxyalkylated) alcohol co-surfactant to make an anti-foaming mixture for the detergent. The claims recite the anti-foaming mixture restrictively, that is, no other components may be present in the claimed anti-foaming mixture except those two elements. No block co-polymers are included in the composition.

A hard surface detergent composition having good spotting and filming characteristics is disclosed by U.S. Pat. No. 5,382,376. The composition includes block polymers. PLURONIC L-62 and other PLURONIC block co-polymers are disclosed for use with the detergent composition. The block co-polymers must be non-ionic surfactants present in amounts between 1–15% and the pH must be between 3 and 12.5. Other components include a hydrophobic cleaning solvent, an aqueous solvent system and a polycarboxylate builder.

A clear, low foam washing agent for dish washers is disclosed by U.S. Pat. No. 3,635,827. The washing agent is formed from a mixture of 70–98% wt. of a water-soluble polyvinyl alcohol having a molecular weight of 1,000–4,000 and from 2–30% wt. of a compound which can be propylene oxide polymers including ethylene oxide.

U.S. Pat. No. 3,388,072 teaches an anti-foaming polymer composition formed from a co-polymerization of ethylene and vinyl acetate. The resulting compound is a polyethylenepolyvinyl alcohol co-polymer. The patent discloses that certain derivatives of the co-polymer have good anti-foaming properties.

Clearly, while some of the prior art patents have disclosed low foaming compositions, they are not adaptable for use in providing a strong fragrance to a water supply in a decorative fountain.

SUMMARY OF THE INVENTION

It is therefore an object of the present invention to provide a recirculating fountain having a non-foaming fragrance in the water used in the fountain.

It is a further object of the invention to provide a non-foaming recirculating fountain which can be used to effectively fragrance an area such as a room without detrimentally affecting the appearance or function of the fountain after extended use.

Yet another object of the invention is to provide a non-foaming fragrant composition for use in a recirculating fountain to fragrance an area such as a room.

Accordingly, compositions are disclosed having either a) a siloxane anti-foam agent and water solution, a block co-polymer, denatured 200 proof alcohol and fragrance oil, b) water, fragrance oil, and siloxane anti-foam agent, and c) an insoluble, non-foaming fragrance oil. The compositions may be provided in a concentrated form, for addition to existing water in recirculating fountain, or in a dilute form for use as the recirculating fluid in the fountain.

The compositions are unexpectedly found to produce 10 times to 50 times the fragrance intensity for the same concentration of fragrance as a gel air freshener. Further, the compositions do not foam when used in a recirculating fountain.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

The only FIGURE in the application is a schematic drawing of a portable fountain using water and the composition according to the invention.

DESCRIPTION OF THE PREFERRED EMBODIMENTS

Referring now to the drawing, in which like reference numerals are used to refer to the same or similar elements, a water fountain 10 has a water supply 20, a pump 30 and a water outlet 40. Water is taken from water supply 20 by pump 30 and delivered to water outlet 40, where the water follows a return path 50 back to the water supply 20. Thus, the water is continuously recirculated. The pump 30 can be used to raise the water to a water outlet 40 located at a point above the water supply 20, so the water can trickle down a return path 50 to the water supply 20. Alternatively, the pump 30 can pressurize the water to spray the water from the water outlet 40 and fall under gravity through the air back into the water supply 20.

In accordance with the invention, the water in the water supply 20 contains at least one of three embodiments of a fragrant non-foaming composition, described in further detail below.

The air freshening compositions of the invention overcome the obstacles found in the prior art to produce a clear, fragrant, water-compatible composition. Each of the three embodiments, A, B and C, provide a variety of ways to incorporate a volatile perfume oil into an aqueous phase.

Test data indicates that the fountain delivery system of 1% by weight perfume oil in the aqueous phase significantly outperforms gel, spray and electric evaporator air freshener devices, even though they contain up to 50 times more (up to 50% wt.) fragrance than the compositions of the invention used in the fountain.

The scented composition can be provided as either a concentrate for adding to an existing fountain water supply, or as a dilute solution for use as the water supply. In a first embodiment, the composition contains a siloxane anti-foam agent and water solution, a block co-polymer, denatured 200 proof alcohol and fragrance oil. The siloxane anti-foam agent is preferably a polydimethylsiloxane and the block co-polymer is preferably an ethylene oxide/propylene oxide block co-polymer which is a non-surface active emulsifier. The dilute, ready to use composition includes a major amount of water. Small amounts of tetrasodium EDTA and citric acid and other sequestering agents can be added to the composition as well as a biocide, such as quaternary ammonium salts.

A second embodiment of the composition solubilizes the fragrance in water with an absence of foaming. The second embodiment of the composition combines a siloxane anti-foam agent like the first embodiment with a solubilized fragrance.

The third embodiment of the fragrant composition consists simply of an insoluble fragrance oil added to the fountain water. The use of an insoluble fragrance oil in the fountain does not cause foaming, while the scent release is also very good.

Surprisingly, it has also been determined that the emulsification or solubilization of perfume oil into the water significantly reduces the fragrance longevity. It has long been established that solubilization of perfume oils into alcohol bases to create single phase colognes and into emulusified creams, lotions and sprays to create fragrant cleaners, personal care products and air fresheners was essential to disperse and distribute the perfume oil uniformly throughout the composition and to maximize an effective does on the skin, hair, fabric surface or in the air.

Test data indicates that the insoluble perfume oil composition matches the intensity of the fragrance provided by the first and second embodiments, but also, unexpectedly, increases the longevity of the fragrance from about 24 hours for the first two embodiments to about 180 hours. Thus, it appears that the insoluble perfume oil dispersed in the fountain water used to fragrance an area creates a more efficient and total release of the fragrance from the fountain, thereby extending the useful life of the product. Thus, a user can add small amounts of insoluble perfume oil to the running water in the fountain in a stepwise fashion to adjust the fragrance level to a personal satsifaction, based on room size and perfume oil volatility.

The following tables show approximate percent weights for each ingredient of the clear concentrated and clear diluted versions of each embodiment of the compositions, respectively:

| Ingredient | Preferred (% wt.) | Range (% wt.) |
|---|---|---|
| Composition A - Concentrate | | |
| 20/80 mixture of polydimethylsiloxane and water (by % weight) | 3.00 | 2–10 |
| Ethylene oxide/propylene oxide block co-polymer | 50.00 | 20–60 |
| Denatured 200 proof alcohol ($C_2$–$C_5$) | 27.00 | 0–30 |
| Fragrance oil | 20.00 | 5–30 |
| TOTAL | 100.00 | 100 |
| Composition A - Dilute Mixture | | |
| Water | 80.70 | q.s. |
| 10/90 mixture of polydimethylsiloxane and water (by % weight) | 0.30 | 0.1–5 |
| Ethylene oxide/propylene oxide block co-polymer | 2.50 | 1–5 |
| Denatured 200 proof alcohol ($C_2$–$C_5$) | 14.50 | 2–20 |
| Fragrance oil | 1.00 | 0.05–5 |
| Citric acid | 0.10 | 0–2 |
| Tetrasodium EDTA | 0.90 | 0–1 |
| TOTAL | 100.00 | 100 |
| Composition B - Concentrate | | |
| Water | 77.00 | 60–93 |
| 20/80 mixture of polydimethylsiloxane and water (by % weight) | 3.00 | 2–10 |
| Solubilized Fragrance oil | 20.00 | 5–30 |
| TOTAL | 100.00 | 100 |
| Composition B - Dilute | | |
| Water | 98.85 | 85–99.94 |
| 20/80 mixture of polydimethylsiloxane and water (by % weight) | 0.15 | 0.01–10.00 |
| Solubilized Fragrance oil | 1.00 | 0.05–5 |
| TOTAL | 100.00 | 100 |
| Composition C - Concentrate | | |
| Water | 80.00 | 70–95 |
| Insoluble Fragrance oil | 20.00 | 5–30 |
| TOTAL | 100.00 | 100 |
| Composition C - Dilute | | |
| Water | 99.00 | 95–99.95 |
| Solubilized Fragrance oil | 1.00 | 0.05–5.00 |
| TOTAL | 100.00 | 100 |

Preferred ingredients for each of the major components include a PLURONIC block co-polymer, such as PLURONIC L-64, from BASF for the ethylene oxide/propylene oxide block co-polymer. PLURONIC L-64 is a non-surface active liquid block co-polymer consisting of 60% by molecular weight of a hydrophobic polypropylene oxide group sandwiched between two hydrophilic ethylene oxide groups. PLURONIC L-61 is also preferred for use. Other non-surface active emulsifier block copolymers that can be used include meroxapol 172, meroxapol 174, meroxapol 252, meroxapol 254, meroxapol 258 and meroxapol 311.

A preferred polydimethylsiloxane is one sold under the identification 1410 by Dow Corning. Other siloxane compounds may be used as well, but are less preferred, including bisphenylhexamethicone, cetyl dimethicone, dimethicone, dimethicone copolyl, dimethicone silylate, dimethiconol, diphenyl dimethicone, hexadecyl methicone, hexamethyldisiloxane, octamethyltrisiloxane, phenethyl disiloxane, phenyl dimethicone, phenyl trimethicone, polysilicone-1, polysilicone-2, polysilicone-7, polysilicone-8, polysilicone-10, silica silylate, simethicone, trimethylsiloxysilicate, triphenyl trimethicone and silicone emulsions including Dow Corning H-10, 2210 and FG-10 silicone emulsions. Preferred usage ranges for these anti-foaming agents is between about 1–100 ppm active silicone. The anti-foaming siloxanes may be diluted with water prior to use in the composition, such as in proportions of 10/90 or 20/80 siloxane to water. Thus, as shown above in the formulas, the actual amount of siloxane is 1/10 to 1/5 of the siloxane/water solution.

Denatured alcohol used in the composition can be SD-39 200 proof alcohol, such as from Remet. The water used is preferably deionized water. Citric acid and tetrasodium EDTA can be obtained from a number of suppliers when they are used.

The composition is a clear, non-foaming, air freshening liquid with very good fragrance release properties. The particular combination of block co-polymers and polydimethylsiloxane, unexpectedly, produces a clear composition which can be mixed in water without changing its appearance.

The block co-polymers have good anti-foaming properties. Anti-foaming refers to the inhibition of formation of foam. The block co-polymer is used to emulsify the fragrance oil, despite the inefficiency—the amount of co-polymer needed to emulsify the fragrance oil is 2.5 times (based on weight) of the amount of fragrance oil.

The polydimethylsiloxane also functions as an anti-foam agent. However, as noted above, polydimethylsiloxanes tend to form cloudy, relatively opaque mixtures when used alone as an anti-foaming agent. It has been found that the combination of the block co-polymer, such as PLURONIC L-64 with a polydimethylsiloxane produces a clear anti-foaming emulsion with the fragrance oil.

When the composition is combined with water to form a clear, non-foaming mixture and used in the environment of a recirculating fountain, a pleasing fragrance can be provided to a relatively large area in strong concentrations. The mixture releases fragrance at least as well or better than other known air freshening devices, such as those presently sold by Bath & Body Works, Inc. In one test, the intensity of the fragrance provided by a recirculating fountain using the composition of the invention was 10 times as great for the same concentration of fragrance as a gel air freshener of a type sold by Bath & Body Works, Inc.

The block co-polymers in the mixture also help to prevent the formation of mineral deposits and water spotting where the water contacts solid surfaces of the fountain. In a further embodiment of the composition, an anti-microbial agent can be added to the composition to prevent growth of pathogens in the fountain as well.

In a preferred use of the compositions, they are added to the recirculating fountain to fragrance a room. The compositions may also be added incrementally to the water supply of a fountain to obtain a desired fragrance level from the scented water. A dropper or other suitable measuring and dispensing device, such as a cup, can be used to incrementally add fragrance to the water supply.

While a specific embodiment of the invention has been shown and described in detail to illustrate the application of the principles of the invention, it will be understood that the invention may be embodied otherwise without departing from such principles.

What is claimed is:

1. A method of fragrancing a room, enclosure or other environment comprising adding a composition comprising 0.5–2% wt. a siloxane anti-foaming agent; up to 20% wt. of a $C_2$–$C_5$ alkanol; 20–60% wt. of a block co-polymer non-surface active emulsifier; 5–30% wt. of a fragrance oil; and water to a recirculating fountain.

2. A method according to claim 1, wherein the block co-polymer non-surface active emulsifier is an ethylene oxide/propylene oxide block co-polymer.

3. A method according to claim 2, wherein the ethylene oxide/propylene oxide block co-polymer is selected from the group consisting of PLURONIC L-61, PLURONIC L-64, meroxapol 172, meroxapol 174, meroxapol 252, meroxapol 254, meroxapol 258 and meroxapol 311.

4. A method according to claim 2, wherein the siloxane is selected from the group consisting of bisphenylhexamethicone, cetyl dimethicone, dimethicone, dimethicone copolyl, dimethicone silylate, dimethiconol, diphenyl dimethicone, hexadecyl methicone, hexamethyldisiloxane, octamethyltrisiloxane, phenethyl disiloxane, phenyl dimethicone, phenyl trimethicone, polysilicone-1, polysilicone-2, polysilicone-7, polysilicone-8, polysilicone-10, silica silylate, simethicone, trimethylsiloxysilicate, triphenyl trimethicone and Dow Corning 1410, H-10, 2210 and FG-10 silicone emulsions.

5. A method according to claim 1, wherein the siloxane anti-foaming agent comprises 2–10% of a solution of siloxane anti-foaming agent and water.

6. A method according to claim 5, wherein the solution contains 10–20% wt. siloxane anti-foaming agent and 80–90% wt. water.

7. A method of fragrancing a room, enclosure or other environment comprising adding a composition comprising 0.01–0.50% wt. of a siloxane anti-foaming agent; 2–20% wt. of a $C_2$–$C_5$ alkanol; 1–5% wt. of a block co-polymer non-surface active emulsifier; 0.05–5% wt. of a fragrance oil; and water to a recirculating fountain.

8. A method according to claim 7, wherein the composition further comprises 0.10–1.00% wt. of a sequestering agent and 0.05–2% wt. of a biocide.

9. A method according to claim 8, wherein the sequestering agent is citric acid and the biocide is tetrasodium EDTA.

10. A method according to claim 7, wherein the block co-polymer non-surface active emulsifier is an ethylene oxide/propylene oxide block co-polymer.

11. A method according to claim 10, wherein the ethylene oxide/propylene oxide block co-polymer is selected from the group consisting of PLURONIC L-61, PLURONIC L-64, meroxapol 172, meroxapol 174, meroxapol 252, meroxapol 254, meroxapol 258 and meroxapol 311.

12. A method according to claim 10, wherein the siloxane is selected from the group consisting of bisphenylhexamethicone, cetyl dimethicone, dimethicone, dimethicone copolyl, dimethicone silylate, dimethiconol, diphenyl dimethicone, hexadecyl methicone, hexamethyldisiloxane, octamethyltrisiloxane, phenethyl disiloxane, phenyl dimethicone, phenyl trimethicone, polysilicone-1, polysilicone-2, polysilicone-7, polysilicone-8, polysilicone-10, silica silylate, simethicone, trimethylsiloxysilicate, triphenyl trimethicone and Dow Corning 1410, H-10, 2210 and FG-10 silicone emulsions.

13. A method according to claim 9, wherein the siloxane anti-foaming agent comprises 2–10% of a solution of siloxane anti-foaming agent and water.

14. A method according to claim 13, wherein the solution contains 10–20% wt. siloxane anti-foaming agent and 80–90% wt. water.

15. A method according to claim 7, wherein the block co-polymer non-surface active emulsifier is an ethylene oxide/propylene oxide block co-polymer.

16. A method according to claim 15, wherein the ethylene oxide/propylene oxide block co-polymer is selected from the group consisting of PLURONIC L-61, PLURONIC L-64, meroxapol 172, meroxapol 174, meroxapol 252, meroxapol 254, meroxapol 258 and meroxapol 311.

17. A composition according to claim 7, wherein the siloxane is selected from the group consisting of bisphenylhexamethicone, cetyl dimethicone, dimethicone, dimethicone copolyl, dimethicone silylate, dimethiconol, diphenyl dimethicone, hexadecyl methicone, hexamethyldisiloxane, octamethyltrisiloxane, phenethyl disiloxane, phenyl dimethicone, phenyl trimethicone, polysilicone-1, polysilicone-2, polysilicone-7, polysilicone-8, polysilicone-10, silica silylate, simethicone, trimethylsiloxysilicate, triphenyl trimethicone and Dow Corning 1410, H-10, 2210 and FG-10 silicone emulsions.

* * * * *